United States Patent [19]

Hirata et al.

[11] Patent Number: 4,708,956

[45] Date of Patent: Nov. 24, 1987

[54] 3-POSITION HALOGENATED CEPHALOSPORIN ANALOGS AND PHARMACEUTICAL COMPOSITIONS

[75] Inventors: Tadashi Hirata, Yokohama; Ikuo Matsukuma, Yokkaichi; Shigeo Yoshiie, Sakai; Kiyoshi Sato; Yoichi Ohashi, both of Shizuoka, all of Japan

[73] Assignee: Kyowa Hakko Kogyo Co., Ltd., Tokyo, Japan

[21] Appl. No.: 896,574

[22] Filed: Aug. 18, 1986

Related U.S. Application Data

[63] Continuation of Ser. No. 807,789, Dec. 12, 1985, abandoned, which is a continuation of Ser. No. 719,640, Apr. 4, 1985, abandoned, which is a continuation of Ser. No. 608,275, May 7, 1984, abandoned, which is a continuation of Ser. No. 389,500, Jun. 17, 1982, abandoned, which is a continuation of Ser. No. 171,297, Jul. 23, 1980, abandoned.

[51] Int. Cl.$^4$ .................... C07D 471/04; C07F 9/65; A61K 31/495; A61K 31/395
[52] U.S. Cl. .................................. 514/210; 540/205
[58] Field of Search ........................ 546/183; 540/205; 514/210

[56] References Cited

U.S. PATENT DOCUMENTS 3,925,372 12/1975 Chauvette ............................. 544/16
4,064,343 12/1977 Chauvette ............................. 544/16
4,123,528 10/1978 Cama et al. ............................ 544/26

FOREIGN PATENT DOCUMENTS

| | | |
|---|---|---|
| 0014475 | 8/1980 | European Pat. Off. . |
| 0014476 | 8/1980 | European Pat. Off. . |
| 2355209 | 5/1974 | Fed. Rep. of Germany . |
| 2714880 | 10/1978 | Fed. Rep. of Germany . |
| 2716707 | 10/1978 | Fed. Rep. of Germany . |
| 2911786 | 9/1979 | Fed. Rep. of Germany . |
| 2911787 | 9/1979 | Fed. Rep. of Germany . |
| 2342974 | 9/1977 | France . |
| 2385722 | 3/1978 | France . |
| 1455016 | 11/1976 | United Kingdom . |
| 2017102 | 10/1979 | United Kingdom . |
| 2017103 | 10/1979 | United Kingdom . |

OTHER PUBLICATIONS

Guth, Konda et al, J. Amer. Chem. Soc., 96, 7584, (1974).
Chauvette et al., J. Amer. Chem. Soc., 96, 4986, (1974).
Chauvette et al, II, Helvetica Chemia Acta, 57, 1919, (1974).

*Primary Examiner*—Mark L. Berch
*Attorney, Agent, or Firm*—Fitzpatrick, Cella, Harper & Scinto

[57] ABSTRACT

Novel cephalosporin analogs are disclosed which have antibacterial activity. Methods for producing the compounds are also disclosed.

18 Claims, No Drawings

3-POSITION HALOGENATED CEPHALOSPORIN ANALOGS AND PHARMACEUTICAL COMPOSITIONS

CROSS REFERENCE TO RELATED APPLICATION

This application is a continuation of application Ser. No. 807,789 filed Dec. 12, 1985, now abandoned which is a continuation of application Ser. No. 719,640 filed Apr. 4, 1985, now abandoned, which is a continuation of application Ser. No. 608,275, filed May 7, 1984, now abandoned, which is a continuation of application Ser. No. 389,500, filed June 17, 1982, now abandoned which is a continuation of application Ser. No. 171,297, filed July 23, 1980, now abandoned.

This application contains subject matter related to copending application Ser. No. 107,435, filed Dec. 26, 1979, abandoned, which copending application pertains to compounds which may be used as intermediates in the preparation of the compounds of the present invention.

BACKGROUND OF THE INVENTION

The present invention relates to novel cephalosporin analogs and more specifically to new carbacephem compounds which differ from cephalosporins by having a carbon atom instead of sulphur atom in the dihydrothiazine ring. In the Journal of the American Chemical Society, 96, 7584 (1974) and J. Med. Chem., 20, 551 (1977) certain carbacephems with substituted methyl groups at the C-3 position such as (i)-1-carbacephalotin represented by the formula:

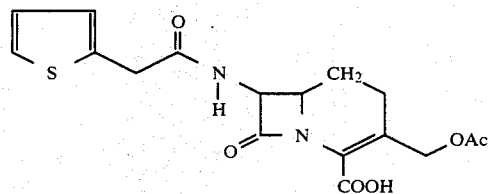

are disclosed as having antibacterial activity. Nevertheless as microorganism populations develop immunity to existing antibiotics new antibacterial compounds are in demand. To this end, novel carbacephems having a hydrogen atom at the C-3 position have been synthesized, such compounds and their synthesis being disclosed in commonly owned U.S. patent applications Ser. No. 23,645 and Ser. No. 23,646, filed Mar. 23, 1979. Furthermore, new carbacephem structures with a halogen atom at C-3 position represented by the formula [II]

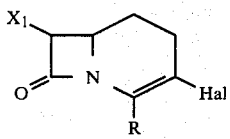

wherein $X_1$ represents an azido, amino or substituted amino group, Hal represents a halogen atom, and R represents a carboxylic acid or a carboxylic acid ester have been synthesized and these compounds and synthesis thereof are disclosed in commonly owed copending U.S. patent application Ser. No. 107,435, filed Dec. 26, 1979. It has now been found that novel 7-acylamino-3-halogen-substituted-carbacephem compounds have unexpectedly potent antibacterial activity.

SUMMARY OF THE INVENTION

In accordance with the present invention, novel carbacephem compounds, i.e. cephalosporin analogs, are synthesized. The nomenclature of "carbacephem" is adopted from the above-mentioned publications.

The present invention includes the carbacephem compounds denominated 7-acylamino-3-halogen-substituted-carbacephem compounds represented by the formula [I]

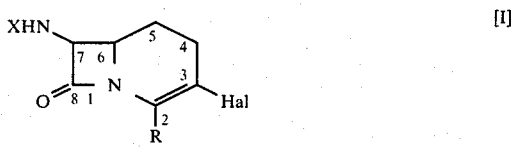

wherein X represents an acyl group, Hal represents a halogen atom, and R represents carboxylic acid or carboxylic acid ester and salts thereof. The numbering system shown in the foregoing formula [I] isused hereinafter.

The invention also pertains to processes for preparing compounds of the formula [I] which comprises acrylating an intermediate represented by formula [II-a]:

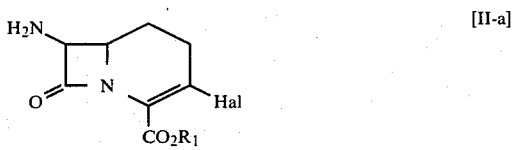

werein Hal has the same meaning as defined above, and $R_1$ represents a hydrogen atom or an ester residue (the aforesaid R is equal to $-COOR_1$).

DETAILED EXPLANATION OF THE INVENTION

The present invention pertains to 7-acylamino-3-halogen-substituted carbacephem compounds as represented by the foregoing formula I. The halogen substituent may be chlorine, bromine and iodine or the like and those compounds having a chlorine substitutent are particularly preferred. The acyl group X is represented by $X_2CO$ and the following five groups are examples of $X_2$.

1. cyanomethyl group or a group represented by the formula:

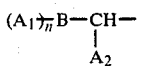

wherein B represents an unsaturated six membered carbocycle, such as a cyclohexenyl group, cyclohexadienyl group, phenyl group, etc. or a five or six membered heterocycle such as a furyl group, thienyl group, pyrrolyl group, thiazolyl group, oxazolyl group, isothiazolyl group, isoxazolyl group, imidazolyl group, pyrozolyl group, triazolyl group, tetrazolyl group, pyridinyl group, pyrimidinyl group, pyrazinyl group, pyridazinyl group, triazinyl group, 5,6-dihydro-1-4-dithiin-2-yl group, etc.; $A_1$ represents a substituent(s) on the B ring which is selected from a hydrogen atom, hydroxyl group, a lower alkoxy group having 1 to 4 carbon atoms, a halo group, nitro group, amino group, aminomethyl group, methylsulfonamido group and a lower acyloxy group having 1 to 4 carbon atoms; n is an integer from 0 to 5; and $A_2$ represents a hydrogen atom, amino group, hydroxyl group, carboxyl group or sulfo group.

2. a group represented by the formula:

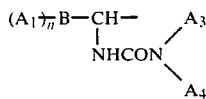

wherein $A_1$, B and n have the same significance as defined above; $A_3$ and $A_4$ are the same or different and represent a hydrogen atom, a lower alkyl group having 1 to 4 carbon atoms, a group represented by the formula:

wherein $A_5$ is a lower alkyl group having 1 to 4 carbon atoms or a group represented by the formula

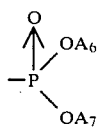

wherein $A_6$ and $A_7$ are the same or different and represent a hydrogen atom, a lower alkyl group having 1 to 4 carbon atoms or an alkali metal; and

also may be a group represented by the formula

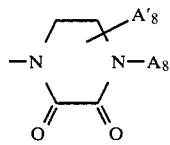

wherein $A_8$ and $A'_8$ are the same or different and are a hydrogen atom or a lower alkyl group having 1 to 4 carbon atoms; or a group represented by the formula

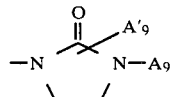

wherein $A_9$ represents a hydrogen atom, a lower alkyl group having 1 to 4 carbon atoms, methylsulfonyl group or furfurylideneimino group, and $A'_9$ represents a hydrogen atom or a lower alkyl group having 1 to 4 carbon atoms.

3. a group represented by the formula:

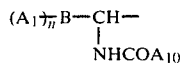

wherein $A_1$, B and n have the same significance as defined above, and $A_{10}$ represents a substituted aryl group or mono-, bi- or tricyclic heterocycles such as a group represented by the formulae:

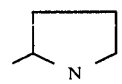

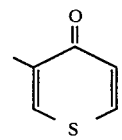

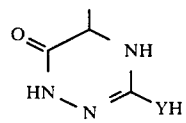

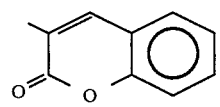

wherein y is oxygen or a sulfur atom, and a naphthyridinyl group such as

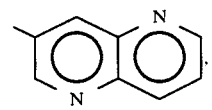

which may have substituents such as those represented by $A_1$ on the rings.

4. a group represented by the formula:

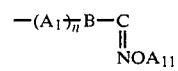

wherein $A_1$, B and n have the same significance as defined above and $A_{11}$ represents a hydrogen atom, a lower alkyl group having 1 to 6 carbon atoms, a lower alkenyl group having 2 to 6 carbon atoms, a lower alkinyl group having 2 to 6 carbon atoms, a cycloalkyl group having 3 to 6 carbon atoms or an aryl group, said $A_{11}$ groups being substituted or unsubstituted with suitable substituent(s) such as carboxyl group, cyano group, a halo group, carbamoyl group or lower alkyloxy-carbonyl group having 1 to 4 carbon atoms.

5. a group represented by the formula:

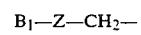

wherein $B_1$ represents a trifluoromethyl group, cyanomethyl group, or a group represented by $(A_1)_n B-$ wherein $A_1$, n and B have the same significance as defined above, and Z represents an oxygen atom or a sulfur atom.

A group represented by R in the general formula [I] (R is —COOR$_1$) is a carboxyl group or a group represented by CO$_2$R'. R' is a carboxy-protecting group employed in the general penicillin and cephalosporin chemistry. That is, an alkyl group having 1 to 5 carbon atoms, such as a methyl group, ethyl group, n-propyl group, isopropyl group, n-butyl group, isobutyl group, sec-butyl, t-butyl group, etc.; a halogenated alkyl group having 1 to 5 carbon atoms, such as a chloromethyl group, 2,2,2-trichloroethyl group, 2,2,2-trifluoroethyl group etc.; an arylmethyl group having 7 to 20 carbon atoms, such as a benzyl group, diphenylmethyl group, triphenylmethyl group, etc.; an arylmethyl group having 7 to 20 carbon atoms and having a methoxy group, nitro group or the like on the phenyl ring; or a substituted silyl group, such as trimethylsilyl group, triphenyl silyl group, etc. are exemplified as R'.

R' may also be a group enzymatically or nonenzymatically readily eliminable in vivo, for example, a group represented by the formula

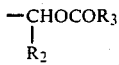

wherein R$_2$ represents a hydrogen atom or a lower alkyl group having 1 to 6 carbon atoms, R$_3$ represents a lower alkyl group having 1 to 6 carbon atoms, a lower alkoxy group having 1 to 6 carbon atoms or phenyl group, or the like.

In the even that R in the formula [I] is a carboxyl group or the acyl group X contains a carboxyl group, a sulfo group, or the like, the compounds represented by the formula [I] may be salts of pharmaceutically acceptable, inorganic or organic bases. In the event that the acyl group X contains an amino group, the compounds represented by the formula [I] may be salts of pharmaceutically acceptable, inorganic or organic acids.

The compounds represented by the formula [I] include all stereoisomers at the 6- and 7-positions and mixtures thereof. Among the stereoisomers, those which have cis-configuration at the 6- and 7-positions have higher antibacterial activity than the trans-isomers and, therefore, the cis-isomers are more desirable as antibiotics.

The =NOA$_{11}$ group in the acyl group has the following two geometrical isomers, i.e. syn and anti.

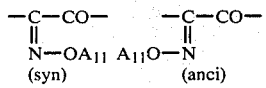

Since the syn-isomer is superior to the anti-isomer in antibacterial activity, the syn-isomer is more desirable as an antibiotic.

In general, it is known that a thiazolyl group represented by

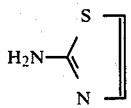

shows reversible interconversion with the thiazolinyl group, as shown below, and both are usually dealt with as identical. In the present specification, both isomers are represented by the thiazolyl group.

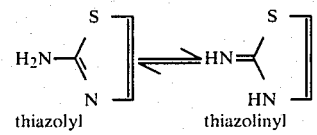

The compounds represented by the formula [I] are produced by acylating compounds represented by the formula [II-a] according to Flow Sheet I.

Flow Sheet I

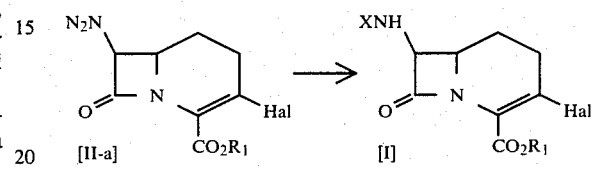

wherein R$_1$, Hal and X have the same significance as defined above.

The acylating reaction (condensation) is carried out according to conventional methods of acylation employed in the field of penicillin and cephalosporin chemistry.

The compounds represented by the formula [I] are prepared by (a) the condensation of the compound represented by the formula [II-a], a salt thereof or a compound functionally equivalent thereto (these are referred to "7-amino compounds" hereinafter) and a carboxylic acid represented by the formula [III]

$$X_3COOH \qquad [III]$$

or a reactive derivative thereof and, if necessary, followed by (b) the deprotection of a protective group in the X$_3$— or —COOR$_1$ group in a conventional manner.

In the formula [III], X$_3$CO— corresponds to X$_2$CO; that is X in the compound represented by the formula [I]; and X$_3$ represents the X$_2$ group defined above or a suitably protected X$_2$ group in the event that X$_2$ has group(s) which are susceptible to acylation, such as an hydroxyl group, amino group, carboxyl group, mercapto group or sulfo group.

X$_3$ represents the following five groups, in particular.

A. cyanomethyl group or a group represented by the formula:

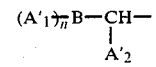

wherein B has the same significance as defined above, A'$_1$ represents a substituent which is selected from a hydrogen atom, hydroxy group, a protected hydroxy group, a lower alkoxy group having 1 to 4 carbon atoms, a halo group, nitro group, a protected amino group, a protected aminomethyl group, methylsulfonamido group and a lower acyloxy group having 1 to 4 carbon atoms; n is an integer from 0 to 5, and A'$_2$ represents a hydrogen atom, a protected amino group, hydroxyl group, a protected hydroxyl group, carboxyl group, a protected carboxyl group, sulfo group or a protected sulfo group.

B. a group represented by the formula:

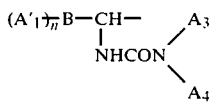

wherein A'$_1$, A$_3$, A$_4$, B and n have the same significance as defined above.

C. a group represented by the formula:

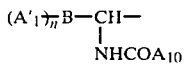

wherein A'$_1$, A$_{10}$, B and n have the same significance as defined above.

D. a group represented by the formula:

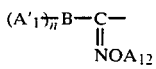

wherein A'$_1$, B and n have the same significance as defined above and A$_{12}$ represents hydrogen or a lower alkyl group having 1 to 6 carbon atoms, a lower alkenyl group having 2 to 6 carbon atoms, a lower alkinyl group having 2 to 6 carbon atoms, a cycloalkyl group having 3 to 6 carbon atoms or an aryl group, these groups being unsubstituted or substituted with substituents, such as a protected carboxyl group, cyano group, a halo group, carbamoyl group or a lower alkyloxycarbonyl group having 1 to 4 carbon atoms.

E. a group represented by the formula:

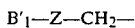

wherein B'$_1$ represents a cyano group, trifluoromethyl group, cyanomethyl group, a group represented by (A'$_1$)$_n$B wherein A'$_1$, n and B have the same significance as defined above, and Z represents an oxygen atom or sulfur atom.

As protecting group(s) for the amino group, hydroxyl group, carboxyl group, mercapto group or sulfo group in the X$_3$ group, those which are typically employed in cephalosporin or penicillin chemistry or in peptide chemistry are used, such as is disclosed in "Protective Groups in Organic Chemistry" by J. F. W. McOmie (Plenum Press, 1973).

As salts of Compound [II-a], inorganic salts and organic salts such as hydrochloride, sulfate, carbonate, phosphate, formate, trifluoroacetate, malate and the like are appropriate. The sodium salt, potassium salt, calcium salt, ammonium salt, organic amine salt, and the like of the carboxylic acid represented by formula [II-a] wherein R$_1$ is hydrogen are appropriate. The salts are prepared according to conventional methods.

As the compound functionally equivalent to Compound [II-a], 7-monosilyl or 7-disilyl amino derivatives of Compound [II-a] are illustrative.

Exemplary of the reactive derivatives of the carboxylic acid represented by formula [III], X$_3$COOH are: (1) an acid halide, (2) an acid anhydride, (3) a mixed acid anhydride, (4) an active ester, (5) an active thioester, and (6) an acid azide, and the like.

Condensation (acylation) reactions using the above derivatives are illustrated as follows.

(1) Method using an Acid Halide

A 7-amino compound and an acid halide are subjected to a condensation reaction in an active solvent and, preferably in the presence of a proton acceptor.

The acid halide is prepared in a conventional manner.

The proton acceptor is, for example an inorganic or organic base and is preferably sodium carbonate, potassium carbonate, sodium hydroxide, potassium hydroxide, triethylamine, N-methylmorphorine, pyridine, and the like.

The solvent is any inactive solvent which does not affect the reaction. Preferably, the solvent is water; an ether such as tetrahydrofuran, dimethoxyethane and the like; an ester such as ethyl acetate; a halogenated hydrocarbon such as methylene chloride, chloroform, and the like; an amide such as dimethylformamide, dimethylacetamide, hexamethylphosphoric triamide; or a sulfoxide, such as dimethylsulfoxide, or mixtures thereof.

The reaction is generally carried out at a temperature of $-20°$ to $40°$ C., preferably from $0°$ C. to room temperature.

(2) Method using an Acid Anhydride

A 7-amino compound and an acid anhydride are subjected to a condensation reaction in an inactive solvent.

The acid anhydride is prepared in a conventional manner.

The solvent is any solvent which does not affect the reaction, and preferably, the same solvents as those in the above method are employed. The range of reaction temperatures is the same as used in the above method.

A typical acid anhydride method uses a carbodiimide, such as dicyclohexylcarbodiimide.

(3) Method using a Mixed Acid Anhydride

A 7-amino compound and a mixed acid anhydride are subjected to a condensation reaction in an inactive solvent.

The mixed acid anhydride is prepared in a conventional manner. For example, a corresponding carboxylic acid, X$_3$COOH, and a chloroformic ester, such as ethyl chloroformate or isobutyl chloroformate are reacted in the presence of a base.

As the solvent, any inactive solvent which does not affect the reaction is employed. Generally, an anhydrous solvent or a mixture of water and an anhydrous solvent and preferably the same solvent as in the above method is utilized.

The range of reaction temperatures is the same as in the above methods.

(4) Method using an Active Ester

A 7-amino compound and an active ester are subjected to a condensation reaction in an inactive solvent.

The solvent and reaction temperatures are the same as those used in the above methods.

As the active ester, a phenylester, such as p-nitrophenyl ester, p-nitrothiophenyl ester, trichlorophenyl ester; a methyl ester having an electronegative group, such as cyanomethyl ester; and N-hydroxydiacylimide ester, such as N-hydroxy-succinimide ester are employed.

The active ester may be prepared in accordance with conventional techniques. For example, a corresponding carboxylic acid and an hydroxyl compound are reacted in the presence of a dehydrating condensation reagent, such as dicyclohexylcarbodiimide to form the active ester.

(5) Method using an Active Thiol ester

This method is carried out in a similar manner as described in the preceding method.

The most preferable thiol ester is p-nitrothiophenyl ester. It is prepared by the mixed acid anhydride method or dicyclohexylcarbodiimide method described hereinabove.

(6) Method using an Acid Azide

A 7-amino compound and an acid azide compound are subjected to a condensation reaction in an inactive solvent in a similar manner as that set forth in the above methods.

The acid azide is prepared by reacting the hydrazide of a corresponding carboxylic acid with nitrous acid at a temperature of $-20°$ to $0°$ C.

In the event the reactive derivatives of the carboxylic acid mentioned above have an amino group, hydroxyl group, carboxyl group, mercapto group or sulfo group susceptible to acylation, these groups are preferably protected with a suitable protecting group prior to the condensation reaction with the amino compounds.

Suitable protecting groups include those used in the field of penicillin and cephalosporin synthetic chemistry.

The amino-protecting group is preferably at t-butyloxycarbonyl group (Boc), benzyloxcarbonyl group (Cbz), trichloroethyloxycarbonyl group, trityl group, formyl group, chloroacetyl group, trialkylsilyl group, proton, β-diketone, β-ketoester, and the like.

As a compound protected with a proton, a compound represented by the formula:

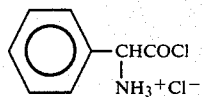

is typical.

As a compound protected with a β-ketoester, a compound represented by the formula:

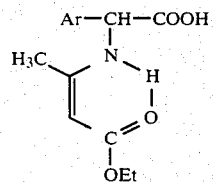

is illustrative.

The hydroxyl-protecting group is usually a benzyl group, benzyloxycarbonyl group, trityl group, tetrahydropyranyl group, t-butyl group and the like. Since the reactivity (nucleophilic activity) of most amino groups is higher than that of the hydroxyl group, protection of the hydroxyl group may not be essential, depending on the acylation method employed.

The carboxyl-protecting group is usually a t-butyl group, benzyl group, p-methoxybenzyl group, p- or o-nitrobenzyl group, benzhydryl group, trityl group or the like.

The mercapto-protecting group may be a benzyl group, trityl group, benzyloxycarbonyl group, p-nitrobenzyl group, or the like.

Introduction and deprotection of the above protecting group is carried out in a conventional method commonly used in the field of the synthetic chemistry of penicillins and cephalosporins or peptides such as the method described in the aforesaid publication entitled "Protective Group in Organic Chemistry".

Various methods of deprotecting amino-protecting groups are utilized. Among them the following conventional techniques are exemplified:

the Boc group is deprotected by a method using an acid, such as formic acid, acetic acid, trifluoroacetic acid, hydrochloric acid, and the like;

the Cbz group is deprotected by catalytic reduction or a method using hydrogen bromide-acetic acid, or the like;

the trityl group is deprotected by a catalytic reduction or a method using an acid, such as trifluoracetic acid, or the like;

the formyl group is deprotected by hydrolysis using an acid or an alkali; the chloroacetyl group is deprotected by a method using thiourea;

the trialkylsilyl group is deprotected by hydrolysis;

a proton is deprotected by neutralization; and the additive with β-diketone or β-ketoester is removed by acid hydrolysis.

To deprotect hydroxyl-protecting groups, the following methods can be employed:

the benzyl group is deprotected by a catalytic reduction or a method using hydrogen fluoride;

the Cbz group is deprotected by a catalytic reduction or a method using hydrogen bromide-acetic acid;

the trityl group is deprotected by a catalytic reduction or a method using trifluoroacetic acid or the like;

the tetrahydropyranyl group is deprotected by acid hydrolysis; and the t-Butyl group is deprotected by a method using an acid such as trifluoroacetic acid, hydrogen bromide-acetic acid, hydrogen chloride or the like.

To deprotect carboxyl-protecting groups, the following techniques are exemplary:

the t-Butyl group is deprotected by a method using an acid such as trifluoroacetic acid;

the benzyl or p- or o-nitrobenzyl group is deprotected by a catalytic reduction or a method using a Lewis acid, such as AlCl$_3$, or the like; o-nitrobenzyl group is also deprotected with light irradiation and the benzhydryl, trityl or p-methoxybenzyl group is deprotected by a catalytic reduction or a method using hydrogen bromide-acetic acid, hydrogen chloride-methanol, trifluoroacetic acid, or the like.

As a method for deprotecting mercapto-protecting groups, the following are exemplified:

the benzyl group is deprotected by a method using hydrogen fluoride or the like;

the Cbz group is deprotected by a method using hydrogen bromide-acetic acid, trifluro-acetic acid, or the like; and the p-Nitrobenzyl group is deprotected by a catalytic reduction.

The deprotection mentioned above may well be carried out concomitantly with the conversion of the R$_1$ group to a hydrogen atom; that is, deesterification.

If desired, the acylating reaction is preferably promoted by silylating the starting compound [II-a] with a silylating agent, such as trimethylchlorosilane-base, hexamethyldisilazane, N,O-bistrimethylsilylacetamide, or the like to solubilize the starting material in an organic solvent and to activate the amino group.

In the preparation of Compound [I], when an optically active Compound [III] or a reactive derivative thereof which has asymmetric carbon atom(s) is used, Compound [I] can be separated into the diastereomers thereof by methods utilizing the differences in the physicochemical properties thereof. Such separating methods include liquid chromatography, chromatography using silica gel, recrystallization and so on. Of these diastereomers, those wherein the configuration of the hydrogens at 6- and 7-positions is represented by the formula

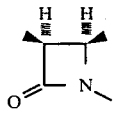

are assumed to have the configuration of (6R, 7S); those having the formula

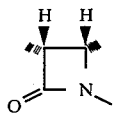

are assumed to have the configuration of (6S, 7R).

The starting compounds represented by the general formula [II-a] can be produced according to the methods described in the specification of Japanese Patent Application No. 162008/78, filed Dec. 26, 1978. The starting compounds can also be produced by the methods disclosed in copending commonly owned U.S. patent application Ser. No. 107,435, filed Dec. 26, 1979. An example is illustrated in Reference Flow Sheet [I].

Reference Flow Sheet [I]

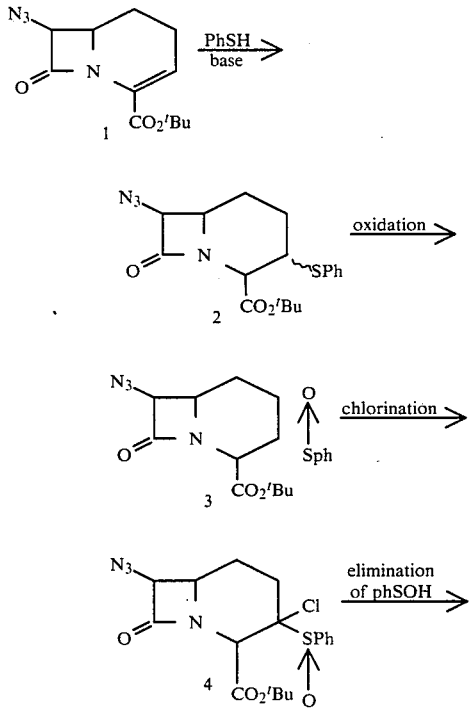

-continued
Reference Flow Sheet [I]

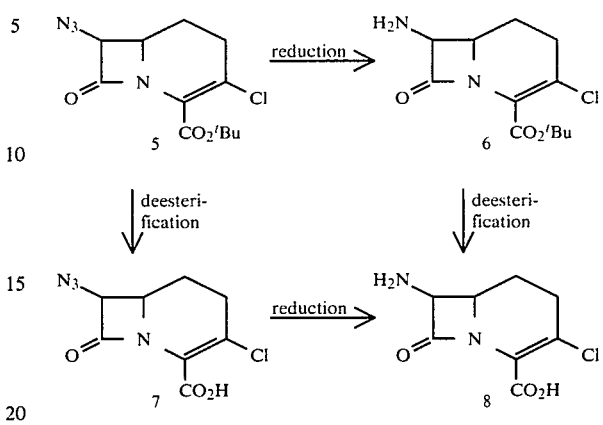

In the foregoing reference flow-sheet, compounds 6 and 8 are examples of the starting compounds for production of the compounds of the present invention. Compound 1 in the reference flow-sheet and methods for production thereof is disclosed in U.S. patent application Ser. No. 23,645, filed on Mar. 23, 1979, and German Offenlegungsschrift No. 2911786. An example is illustrated in the following Reference Flow Sheet [II].

Reference Flow Sheet [II]

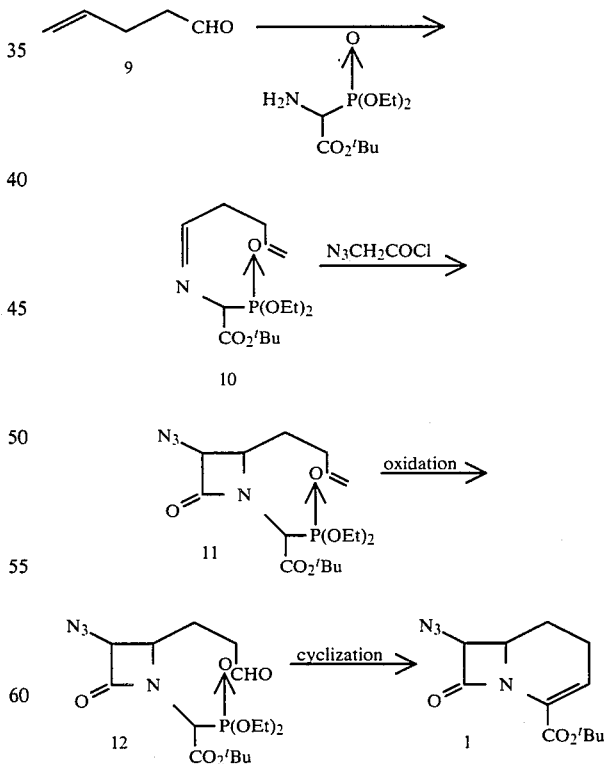

Compound [I'] represented by the formula [I] wherein R is a carboxyl group can be produced by elimination of the carboxyl-protecting group according to the process shown in Flow Sheet [II].

Flow Sheet [II]

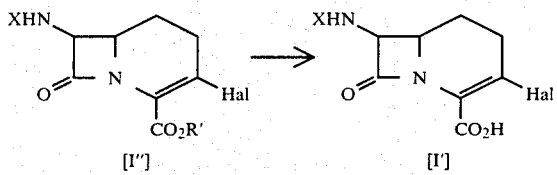

wherein R' is a protecting group for a carboxyl group and Hal and X have the same significance as defined above.

The deesterification reaction is carried out according to conventional methods employed in the synthetic chemistry art for penicillins and cephalosporins.

Suitable reactions which convert the —COOR' group to a —COOH group include: (1) catalytic reduction; (2) acidolysis; (3) cleavage reaction using a Lewis acid; (4) hydrolysis; (5) reduction other than catalytic reduction using reducing agents; (6) photochemical cleavage; (7) electrolytic cleavage and (8) a method using an esterase, each of which are described below.

1. Catalytic reduction

In this reaction the COOR' group is converted to a COOH group in the presence of a catalyst in a hydrogen atmosphere and in an inactive solvent. As the solvent, any solvent which does not affect the reaction and preferably ethanol, water, tetrahydrofuran, dioxane, ethyl acetate, or acetic acid, may be used alone or in combination. As the catalyst, palladium-carbon, platinum oxide, palladium-calcium carbonate and Raney nickel are suitable. The reaction is carried out generally at a pressure of 1 to 50 atmospheres and a temperature of 0° to 100° C., preferably at atmospheric pressure and room temperature.

This method is preferably employed when R' is a benzyl group, p-nitrobenzyl group, diphenylmethyl group, p-methoxybenzyl group, or the like.

2. Acidolysis

In this reaction the COOR' group is converted to a COOH group with an acid in an inactive solvent. As the acid, hydrogen chloride, p-toluenesulfonic acid, trifluoroacetic acid, and the like are used. As the solvent, any solvent which does not affect the reaction, and preferably ethyl acetate, benzene, ethanol, acetic acid, dioxane, methylene chloride or chloroform, may used alone or in combination.

The reaction is carried out at a temperature of 31 15° to 50° C., preferably 0° to 25° C., for 10 minutes to 5 hours, preferably 30 minutes to 3 hours.

This method is preferred when R' is a t-butyl group, trityl group and so on.

3. Cleavage reaction using a Lewis acid

In this reaction the COOR' group is converted to a COOH group by cleavage in the presence of a Lewis acid in an inactive solvent, such as any solvent which does not affect the reaction, preferably a mixture of a nitroalkane such as nitromethane and a haloalkane such as methylene chloride. As the Lewis acid, aluminum chloride, boron trifluoride, titanium tetrachloride, tin tetrachloride, and the like are used. The acid is used in an amount of 1.0 to 1.5 molar equivalents to Compound [I'']. The reaction is preferably carried out in the presence of an agent which takes up carbonium cation, such as anisole. The reaction is carried out at a temperature of 0° to 50° C., preferably at room temperature for 1 to 10 hours.

This method is preferred when R' is a benzyl or p-nitrobenzyl group and so on.

4. Hydrolysis

In this reaction the COOR' group is converted to a COOH group by hydrolysis in the presence of an acid or alkali in an inactive solvent. Suitable acids include p-toluenesulfonic acid, hydrochloric acid, acetic acid, and the like. Any solvent which does not affect the reaction may be used and preferably 2% aqueous methanol, N,N-dimethylformamide or acetic acid-water-tetrahydrofuran, are employed. The reaction is generally carried out at a temperature of 0° to 50° C., preferably 15° to 25° C. for 10 minutes to 2 hours.

This method utilizing an acid is preferred when R' is a t-butyldimethylsilyl group.

As the alkali, calcium carbonate is preferably used in an amount of 1 to 6 molar equivalents to Compound [I'']; and any solvent which does not affect the reaction, preferably tetrahydrofuran-water, dioxane-water or acetone-water, is used. The reaction is generally carried out at a temperature of 0° to 30° C. for 30 minutes to 24 hours.

This method utilizing an alkali is preferred when R' is a methyl group, ethyl group and so on.

5. Reduction using reducing agents (other than catalytic reduction)

In this reaction the COOR' group is converted to a COOH by reduction in an inactive solvent, for example, using a zinc-acid. For this reason a solvent such as acetone water, dioxane, tetrahydrofuran, ethanol, acetonitrile, N,N-dimethylformamide and acetic acid may be used alone or in combination. As the acid, hydrochloric acid, formic acid and acetic acid are suitable. The reaction is carried out at a temperature of 0° to 100° C., preferably 0° to 40° C. for 1 to 10 hours. The amount of zinc used for the reaction is usually 1 to 10 molar equivalents. This method is preferred when R' is 2,2,2-trichloroethyl or 2,2,2-trifluoroethyl group and so on.

If appropriate reagents are employed, the protecting group in group X can be eliminated simultaneously with deesterification.

The compounds of the present invention represented by formula [I] wherein R is a carboxyl group, provide excellent antibacterial activity against Gram-positive and Gram-negative bacteria and they are expected to be useful as antiinfectional agents or antibacterial agents against these bacteria. The compounds represented by the general formula [I], wherein R is other than a carboxyl group, may also be used as the starting material for the compounds represented by the general formula [I] wherein R is a carboxyl group.

The invention includes, wherein its scope, pharmaceutical compositions comprising, as an active ingredient, Compound [I] or a pharmaceutically acceptable salt thereof in association with a pharmaceutical carrier or diluent. The compounds of this invention may be administered by parenteral (intramuscular, intraperitioneal, intravenous, or subcutaneous injection routes), oral or rectal routs; and can be formulated in dosage forms appropriated for each route of administration.

Preparations according to this invention for parenteral administration include sterile aqueous or non-aqueous solutions, suspensions, or emulsions. Examples of non-aqueous solvents or vehicles for such solutions, suspensions or emulsions are propylene glycol, polyethylene glycol, vegetable oils, such as olive oil, and injectable organic esters, such as ethyl oleate. Such dosage forms may also contain adjuvants such as preserving, wetting, emulsifying, and dispersing agents. Preparations may be sterilized by filtration through a bacteria-retaining filter, by incorporation of sterilizing agents into the compositions, by irradiation of the compositions, or by heating the compositions. Dosage forms can also be manufactured in the form of sterile solid compositions which can be dissolved in sterile water, or some other sterile injectable medium immediately before use.

Compositions for oral administration may be presented in a form suitable for absorption by the gastrointestinal tract. Tablets and capsules for oral administration may be in unit dose presentation form. They may contain conventional excipients such as binding agents, for example, syrup, acacia, gelatin, sorbitol, tragacanth, or polyvinylpyrrolidone; fillers, such as, lactose, sugar, maize-starch, calcium, phosphate, sorbitol or glycine; lubricants, for example, magnesium stearate, talc, polyethylene glycol, sialica; disintegrants such as potato starch or acceptable wetting agents, such as sodium lauryl sulphate. The tablets may be coated according to methods well known in the art. Oral liquid preparations may be in the form of aqueous or oily suspensions, solutions, emulsions, syrups, or the like. Alternatively, preparations may be provided as a dry product for reconstitution with water or other suitable vehicles before use. Such liquid preparations may contain conventional additives such as suspending agents, including soribtal syrup, methyl cellulose, glucose sugar-syrup, gelatin, hydroxyethylcellulose, carboxymethylcellulose, aluminum stearate gel; emulsifying agents, for example, lecithin or sorbitan monooleate; non-aqueous vehicles, including edible oils (such as almond oil or coconut oil), propylene glycol, or ethyl alcohol; preservatives, for example, methyl or propyl p-hydroxybenzoates or sorbic acid.

Compositions for rectal administration are preferably suppositories which may contain, in addition to the active substance, excipients such as cocoa butter or a suppository wax.

The dosage of active ingredients, in the compositions of this invention may be varied; however, sufficient amounts of the active ingredient(s) are employed to obtain a suitable dosage form. The selected dosage depends upon the desires therapeutic effect, on the route of administration, and on the duration of the treatment. Generally, dosage levels of between about 5 to 350 mg/kg of body weight daily are administered to mammalian patients to achieve an antibiotic effect.

As pharmaceutically acceptable salts of Compound [I], inorganic salts and organic salts such as hydrochloride, sulfate, carbonate, phosphate, formate, malate, etc. are suitable. Additionally, the sodium salt, potassium salt, calcium salt, ammonium salt, organic amine salt, etc. of the carboxylic acid represented by the general formula [I] wherein R is a carboxyl group are appropriate. These salts may be prepared by conventional methods.

Certain specific embodiments of the invention are illustrated by the following representative examples.

EXAMPLE 1

Preparation of the t-butyl ester of (±)-cis-7-(2-phenyl-2-t-butyloxycarbonyl-aminoacetamido)-3-chloro--1-azabicyclo[4,2,0]oct-2-en-8-one-2-carboxylic acid:

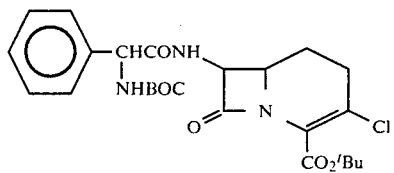

As used herein, "cis" means the cis-configuration at the 6- and 7-positions.

In this example, 150 mg (0.55 mmole) of (±)-cis-7-amino-3-chloro-2-t-butyloxycarbonyl-1-azabicylo[4,2,0]oct-2-en-8-one is dissolved in 3 ml of anhydrous methylene chloride. In a separate vessel, 166 mg (0.66 mmole) of (R)-N-t-butyloxycarbonyl-phenylglycine is dissolved in 5 ml of anhydrous tetrahydrofuran and the solution is cooled to −15° to −10° C. Then, 0.66 ml (0.66 mmole) of 1N-N-methyl-morpholine-tetrahydrofuran and 0.66 ml (0.66 mmole) of 1N-$^i$Bu chloroformate-tetrahydrofuran are added dropwise and the mixture is stirred at the same temperature for 20 minutes. The above-prepared amine solution is then added dropwise to the mixture while maintaining the same temperature and, thereafter, the temperature of the mixture is gradually raised to room temperature. The mixture is stirred at room temperature overnight after which 10 ml of methylene chloride is added and the mixture is washed with 10% citric acid, saturated aqueous sodium bicarbonate and saturated aqueous sodium chloride in this order, and dried with anhydrous sodium sulfate. The mixture is concentrated under reduced pressure and purified by silica gel chromatography (silica gel; 20 g of C-200 produced by Wako Junyaku Co., Ltd., Japan, solvent; ethyl acetate:n-hexane=1:5 by volume, which is also used hereinafter) to obtain 124 mg (yield 44.6%) of the desired compound (mixture of the diasteroisomers) having the following properties.

IR(KBr)$\nu_{max}^{cm-1}$: 1780, 1730, 1680, 1655, 1550

NMR(CDCl$_3$)δ(ppm): 7.34(5/2H,s), 7.31(5/2H, s) 6.93(1H, m), 5.63(1H, m), 5.30 (1/2H, dd, J=5.4, 6.8 Hz,) 5.11–5.22(3/2H, m), 3.76–3.91 (1H, m), 2.33–2.66(2H, m), 1.52(9H, s), 1.41(9H, s), 0.92–1.97(2H, m)

EXAMPLE 2

Preparation of (6R, 7S) 7-(R)-phenylglycinamido-3-chloro-1-azabicyclo[4,2,0]oct-2-en-8-on-2-carboxylic acid (A) and (6S, 7R) 7-(R)-phenylglycinamido-3-chloro-1-azabicylo[4,2,0]oct-2-en-8-on-2-carboxyl acid (B):

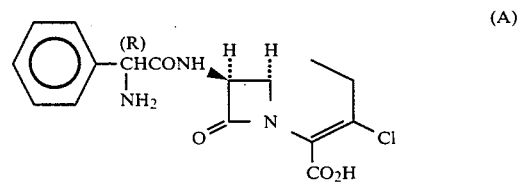

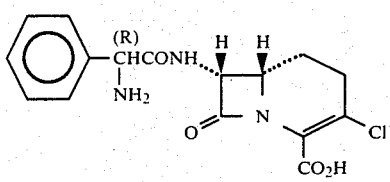

In this example, 1 ml of methylene chloride and 1 ml of trifluoroacetic acid are added to 128.4 mg (0.25 mmole) of t-butyl ester of (±)-cis-7-(R)-(2-phenyl-2-t-butyloxycarbonylaminoacetamido)-3-chloro-1-azabicyclo[4,2,0]oct-2-en-8-on-2-carboxylic acid under ice cooling and the mixture is stirred at the same temperature for 1.5 hours. The solvent is distilled off and the resultant oily material is subjected to high speed liquid chromatography [column: Microbondapak C-18 (product of Waters Co.), solvent: 7% methanol and 0.2N $KH_2PO_4$] tp separate diastereoisomers. Each separated eluate fraction is concentrated under reduced pressure and desalted using 10 ml of HP-10 resin (product of Mitsubishi Kasei Co., Ltd) (solvent; methanol:-water=1:1) to obtain 9.4 mg of the more polar isomer (B) and 7.6 mg of the less polar isomer (A) (total yield 19.1%).

More polar isomer (B):
$[\alpha]_D^{21°}$: $-75.8°$ (c=0.4, $H_2O$)
Melting point: 300° C. or more (browning)
IR(KBr)$\nu_{max}^{cm-1}$: 1765, 1700, 1550
NMR($D_2O$)$\delta$(ppm): 7.49(5H, s), 5.16(1H, d, J=4.7 Hz), 5.05(1H, s), 3.78-4.03(1H, m), 2.53-2.67(2H, m), 1.26-2.09(2H, m)

Less polar isomer (A):
$[\alpha]_D^{21°}$: $+34.0°$ (c=0.35, $H_2O$)
Melting point: 300° C. ore more (browning)
IR(KBr)$\nu_{max}^{cm-1}$: 1770, 1700, 1620
NMR($D_2O$)$\delta$(ppm): 7.51(5H,s), 5.36(1H, d J=4.6 Hz), 5.19(1H, s), 3.38-4.00(1H, m), 2.41-2.56(2H, m), 1.49-1.76(1H, m), 1.14-1.45(1H,m)

As is described below, the less polar isomer (A) exhibits greater antimicrobial activity and is assigned the (6R, 7S) absolute configuration.

EXAMPLE 3

Preparation of the t-butyl ester of cis-7-[(R)-2-phenyl-2-(4-ethyl-2,3-dioxopiperadinylcarbonylamino)acetamido]-3-chloro-1-azabicylo[4,2,0]oct-2en-8-on-2-carboxylic acid:

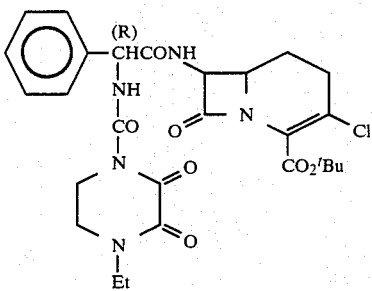

In this example, 351 ml (1.1 mmole) of N-(4-ethyl-2,3-dioxopiperadinylcarbonyl)-(R)-phenylglycine is dissolved in 10 ml of anhydrous tetrahydrofuran. Then 1.2 ml of 1N N-methylmorpholine-tetrahydrofuran and 1.1 ml of 1N$^i$Bu chloroformate-tetrahydrofuran are added at $-15°$ to $-10°$ C. and the mixture is stirred at the same temperature for 30 minutes. To the mixture, 10 ml of methylene chloride solution containing 309 mg (1 mmole) of t-butyl ester of cis-7-amino-3-chloro-1-azabicyclo[4,2,0]oct-2-en-8-on-2-carboxylic acid hydrochloride and 1N N-methylmorpholinetetrahydrofuran is added dropwise while maintaining the temperature at $-15°$ to $-10°$ C. The temperature of the mixture is then raised gradually to room temperature and the mixture is stirred at this temperature overnight. The mixture is concentrated under reduced pressure and ethyl acetate is added thereto. The solution is then washed with 10% citric acid, saturated aqueous sodim bicarbonate and saturated aqueous sodium chloride in this order and dried with anhydrous sodium sulfate. The solvent is distilled off under reduced pressure to obtain 273 mg (47.6%) of the desired compound (mixture of diastereoisomers). The compound is subjected to silica gel chromatography (silica gel; 30 g, solvent; ethyl acetate:n-hexane=3:2) to separate the diastereoisomers whereby 78.4 mg of the less polar isomer and 112 mg of the more polar isomer are obtained. Less polar isomer;

$[\alpha]_D^{21°}$: $-4.4°$ (c=0.5, MeOH)
Melting point: 181°-183° C. (decomposition)
IR(KBr)$\nu_{max}^{cm-1}$: 1790, 1730, 1685, 1525
NMR(CDCl$_3$)$\delta$(ppm): 9.90(1H, d, J=6.3 Hz), 7.28-7.35 (5H, m), 7.17(1H, d, J=6.8 Hz), 5.46(1H, d, J=6.3 Hz), 5.33(1H, dd, J=4.9, 6.8 Hz), 3.66-4.15(3H, m), 3.41-3.62(4H, m), 2.41-2.56(2H, m), 1.51(9H, s), 0.88-1.76(2H, m), 1.21 (3H, t, J=7.3 Hz)

More polar isomer:
$[\alpha]_D^{21°}$: $-53.0°$ (c=0.5, MeOH)
Melting point: 159°-170° C. (decomposition)
IR(KBr)$\nu_{max}^{cm-1}$: 185, 1725, 1700, 1685, 1525
NMR(CDCl$_3$)$\delta$(ppm): 9.86(1H, d, J=6.3 Hz), 7.35(5H, s), 7.06(1H, d, J=6.4 Hz), 5.42(1H, d, J=6.3 Hz), 5.19(1H, dd, J=4.9, 6.4 Hz), 3.75-4.15(3H, m), 3.45-3.66(4H, m), 2.50-2.63(2H, m), 0.88-2.44(2H, m), 1.51(9H, s), 1.22(3H, t, J=7.3 Hz)

EXAMPLE 4

Preparation of (6R, 7S) 7-[(R)-2-phenyl-2-(4-ethyl-2,3-dioxopiperadinylcarbonylamino)-acetamido]-3-chloro-1-azabicyclo[4,2,0]oct-2-en-8-on-2-carboxylic acid:

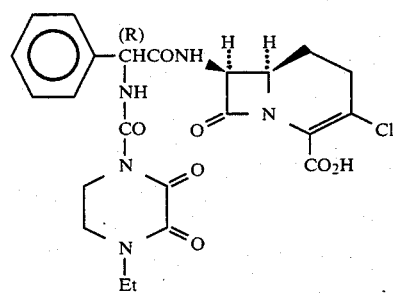

In this example, 50 mg of the less polar isomer synthesized according to Example 3 is dissolved in 25 ml of anhydrous methylene chloride and 2.5 ml of trifluoroacetic acid is added thereto under ice cooling. The mixture is stirred at the same temperature for 4 hours and the solvent is then distilled off under reduced pressure. The residue is purified by silica gel chromatography (silica gel; 5 g, solvent, chloroform:methanol=20:1) to obtain 22 mg (48.8%) of the desired compound.

[α]$_D^{21°}$: −1.2° (c=0.5, MeOH)

Melting point: 175°–190° C. (slow decomposition)

IR(KBr)$\nu_{max}^{cm-1}$: 1780, 1720, 1685, 1520

NMR(CDCl$_3$—CD$_3$OD)δ(ppm): 7.31–7.48(5H, m), 5.45(1H, s), 5.32(1H, d, J=4.9 Hz), 3.75–4.29(3H, m), 3.44–3.65(4H, m), 2.44–2.53(2H, m), 1.15–2.20(2H, m), 1.23(3H, t, J=7.3 Hz)

EXAMPLE 5

Preparation of (6S, 7R) 7-[(R)-2-phenyl-2-(4-ethyl-2,3-dioxopiperadinylcarbonylamino)acetamido]-3-chloro-1-azabicyclo[4,2,0]oct-2-en-8-on-2-carboxylic acid:

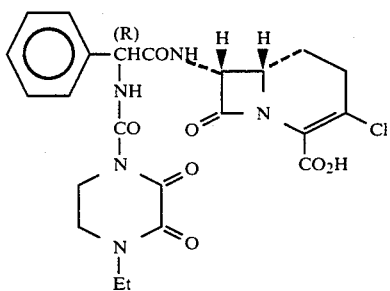

In this example, the procedure described in Example 4 is repeated except that 50 mg of the more polar isomer synthesized according to Example 3 is used to obtain 17.7 mg (39.2%) of the desired compound.

[α]$_D^{21°}$: −50.6° (c=0.52, MeOH)

IR(KBr)$\nu_{max}^{cm-1}$: 1780, 1720, 1680, 1520

NMR(CDCl$_3$-CD$_3$OD)δ(ppm): 7.31–7.48(5H, m), 5.37(1H, s), 5.21(1H, d, J=4.9 Hz), 3.79–4.08(3H, m), 3.44–3.65(4H, m), 2.61–2.69(2H, m), 1.11–2.07(2H, m), 1.23(3H, t, J=7.3 Hz)

EXAMPLE 6

Preparation of (±)cis-7-phenylacetamido-3-chloro-1-azabicyclo[4,2,0]oct-2-en-8-on-2-carboxylic acid

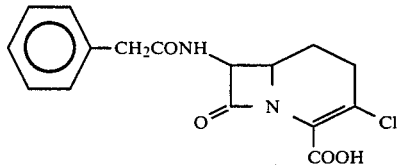

In this example, 150 mg (0.45 mmole) of trifluoroacetate of (±)-cis-7-amino-3-chloro-1-azabicyclo[4,2,0]oct-2-en-8-on-2-carboxylic acid is suspended in a mixed solvent of 2 ml of water and 2 ml of acetone, to which 134 mg (1.5 mmole) of sodium bicarbonate is added to make up a homogenous solution. To the solution, a solution of 84.2 mg (0.54 mmole of phenylacetyl chloride in 0.5 ml of acetone is added dropwise under ice cooling in one hour. The mixture is stirred for 3 hours, adjusted to pH 2 with 1N hydrochloric acid and extracted 5 times with 2 ml of ethyl acetate. The extract is concentrated under reduced pressure and the residue is dried to obtain 80 mg (55.0%) of the desired compound.

IR(KBr)$\nu_{max}^{cm-1}$: 1790, 1705, 1630, 1560

NMR(CD$_3$OD)δ(ppm): 7.29(5H, s), 5.36(1H, d, J=5 Hz), 3.79–3.99(1H, m), 2.56–2.75(2H, m), 1.17–2.02(2H, m)

EXAMPLE 7

Preparation of cis-7-[2-(2-furyl)-2-syn-methoxyiminoacetamido]-3-chloro-1-azabicyclo[4,2,0]oct-2-en-8-on-2-carboxylic acid

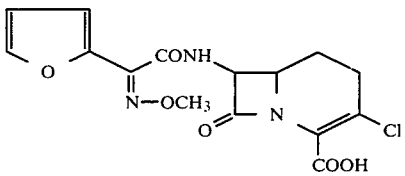

In this example, 37.9 mg (0.224 mmole) of 2-(2-furyl)-2-syn-methoxyiminoacetic acid is dissolved in absolute methanol. Then, 344 μl of 0.65N sodium methylate-methanol is added thereto to obtain the sodium salt thereof and the solvent is distilled off under reduced pressure. The residue is dried in vacuo to obtain a powder which is then suspended in 1 ml of anhydrous benzene and one drop of anhydrous dimethylformamide. Thereafter, 29 μl (0.336 mmole) of oxalyl chloride is added and the mixture is stirred at room temperature for one hour. The mixture is then concentrated under reduced pressure and 2 ml of anhydrous tetrahydrofuran is added to prepare an acid chloride solution.

In a separate vessel, 1.6 ml of tetrahydrofuran and 1.6 ml of water are added to 57 mg (0.72 mmole) of the trifluoroacetate of cis-7-amino-3-chloro-1-azabicyclo[4,2,0]oct-2-en-8-on-2-carboxylic acid. To this solution, 120 μl (0.862 mmole) of triethylamine is added under ice cooling to prepare a homogenous solution. The the acid chloride solution is added dropwise to the solution and the mixture is stirred under ice cooling for one hour. The mixture is adjusted to pH 2 with 1N hydrochloric acid and extracted with ethyl acetate. The extract is washed with saturated aqueous sodium chloride, dried with anhydrous sodium sulfate and concentrated under reduced pressure. The concentrate is dried in vacuo to obtain 86.8 mg of the desired compound as a crude powder. The crude powder is recrystallized from chloroform to obtain 29.6 mg (46.7%) of white crystals.

Melting point: 134°–137' C. (decomposition)

IR(KBr)$\nu_{max}^{cm-1}$: 1780, 1720, 1655, 1620, 1545

NMR(CDCl$_3$-CD$_3$OD)δ(ppm): 7.54(1H, d, J$_{32}$ 1.7 Hz), 6.73(1H, d, J=3.7 Hz), 6.56(1H, dd, J=1.7, 3.7 Hz), 5.47(1H, d, J=4.9 Hz), 4.01(3H, s), 3.90–4.13(1H, m), 2.65–2.79(2H, m), 1.70–2.20(2H, m)

EXAMPLE 8

Preparation of (±)-cis-7-[2-(2-chloroacetamidothiazole-4-yl)-2-syn-methoxyiminoacetamido]-3-chloro-1-azabicyclo[4,2,0]oct-2-en-8-on-2-carboxylic acid:

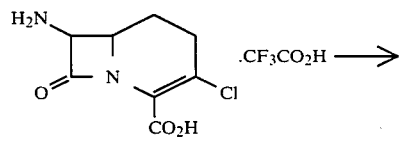

-continued

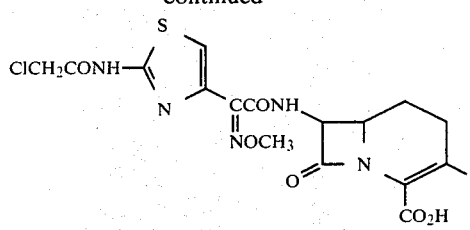

In this example, 122.6 mg (0.44 mmole) of 2-(2-chloroacetamidothiazole-4-yl)-2-syn-methoxyiminoacetic acid is dissolved in 2.5 ml of anhydrous methylene chloride. Then, 68 μl (0.49 mmole) of triethylamine is dissolved and 92.9 mg (0.44 mmole) of phosphorous pentachloride is added under cooling with an ice-sodium chloride mixture. The mixture is stirred at that temperature for one hour and then 5 ml of n-hexane is added thereto. This mixture is stirred under ice cooling for 15 minutes. The separated oily material is obtained by removing n-hexane by decantation. The oily material is dissolved in 4 ml of tetrahydrofuran to prepare an acid chloride solution. In a separate vessel, 121.7 mg (0.37 mmole) of the trifluoroacetate of (±)-7-amino-3-chloro-1-azabicyclo[4,2,0]oct-2-en-8-on-2-carboxylic acid is dissolved in 50% aqueous tetrahydrofuran and 0.2 ml (1.47 mmole) of triethylamine. To this solution, the above-prepared acid chloride solution in tetrahydrofuran is added with stirring under ice cooling. The mixture is stirred at that temperature for one hour and adjusted to pH 3 with 1N hydrochloric acid. Water is added thereto and the mixture is extracted with ethyl acetate. The extract is washed with saturated aqueous sodium chloride and dried with anhydrous sodium sulfate. The solvent is adequately distilled off to obtain 53.9 mg (30.5%) of the desired compound as a powder.

IR(KBr)$v_{max}^{cm-1}$: 1770, 1680, 1555, 1045

NMR(DMSO-$d_6$)δ(ppm): 9.38(1H, d J=8 Hz), 7.37(1H, s), 5.45(1H, q, J=5, 8 Hz), 4.35(2H, s)

EXAMPLE 9

Preparation of (±)-cis-7-[2-(2-aminothiazole-4-yl)-2-syn-methoxyiminoacetamido]-3-chloro-1-azabicyclo[4,2,0]oct-2en-8-on-2-carboxylic acid:

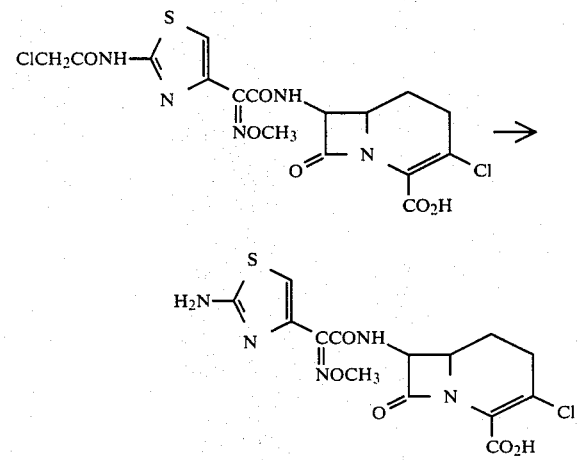

In this example 51.2 mg (0.11 mmole) of the chloroacetamido compound obtained in Example 8 is dissolved in 1 ml of dimethylacetamide and then 16.3 mg (0.22 mmole of thiourea is added. The mixture is stirred at room temperature for 14 hours after which 7 ml of ether is added and the stirring is continued for an additional 10 minutes. The separated oily material is obtained by removing the ether by decantation. The oily material is dissolved in a small amount of dimethylsulfoxide, absorbed on 10 ml of HP-10 in a column and eluted with dimethylsulfoxide. The eluate is twice treated with HP-10 resin [eluent:watermethanol (amount of methanol is gradually increased and finally elution is carried out with water:methanol=1:1)] to obtain 1.52 mg (35.4%) of the desired compound.

Melting point: 185.0°–188.0° C. (decomposition)

IR(KBr)$v_{max}^{cm-1}$: 1765, 1670, 1630, 1540, 1040

NMR(DMSO-$d_6$)δ(ppm): 9.28(1H, d J=8.8 Hz), 7.17(2H, s), 6.75(1H, s), 5.44(1H, q, J=5.3, 8.8 Hz), 3.84(3H, s), 1.24–2.52(4H, m)

EXAMPLE 10

Preparation of (6R, 7S) 7-(R)-p-hydroxyphenylglycinamido-3-chloro-1-azabicyclo[4,2,0]oct-2-en-8-on-2-carboxylic acid:

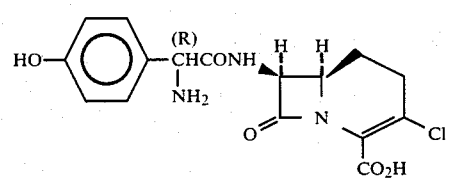

In this example, 1 ml of methylene chloride and 1 ml of trifluoroacetic acid are added under ice cooling to 104.3 mg (20 mmole) of t-butyl ester of (±)-cis-7-[2-(P-hydroxyphenyl)-2-t-butyloxycarbonylaminoacetamido]-3-chloro-1-azabicylo[4,2,0]oct-2-en-8-on-2-carboxylic acid (mixture of the diastereoisomers) synthesized form t-butyl ester of (±)-cis-7-amino-3-chloro-1-azabicyclo[4,2,0]oct-2-en-8-on-2-carboxylic acid and N-t-butyloxycarbonyl-(R)-p-hydroxyphenylclycine. The mixture is stirred at the same temperature for 1.5 hours and then concentrated under reduced pressure. The resultant oily material is subjected to high speed liquid chromatography (column: Microbondapak C-18, solvent: 7%-methanol-0.2N potassium dihydrogen phosphate) to separate the diastereoisomers. Fractions containing the less polar isomer are concentrated under reduced pressure and desalted with 10 ml of HP-10 rein (solvent, methanol:water=1:1) to obtain 10.5 mg (28.7%) of the desired compound.

$[α]_D^{20°}$: +44° (c=0.25, 1M phosphate buffer, pH 7.0)

IR(KBr)$v_{max}^{cm-1}$: 1765, 1695, 1615, 1520

NMR($D_2O$)δ(ppm): 7.36(2H, d, J=8.8 Hz), 6.96(2H, d, J=8.8 Hz), 5.36(1H, d, J=4.6 Hz), 5.11(1H, s), 3.81–4.00(1H, m), 2.42–2.58(2H, m), 1.59–1.77(1H, m), 1.17–1.48(1H, m)

The antibacterial activity of the compounds obtained in Examples 2, 4, 7, 9 and 10 is shown in the following table. The activity is determined by the Heart Infusion Agar Dilution Method (pH 7.2). Cephalexin and cefazolin are used as reference compounds, and the activity thereof is also set forth in the table.

| Microorganism | Minimum Inhibitory Concentration (μg/ml) | | | | | | |
|---|---|---|---|---|---|---|---|
| | a | b | c | d | e | f | g |
| Staphylococcus aureus 209-p | 0.1 | 0.4 | 6.25 | 50 | 0.4 | 0.2 | ≦0.05 |
| Staphylococcus aureus Smith | 1.56 | 1.56 | 12.5 | 50 | 1.56 | 3.12 | 0.4 |
| Staphylococcus epidermidis | 1.56 | 1.56 | 25 | 50 | 1.56 | 3.12 | 0.78 |
| Escherichia coli NIHJC-2 | 1.56 | 3.12 | 50 | 0.78 | 1.56 | 12.5 | 1.56 |
| Escherichia coli Juhl | 1.56 | 3.12 | 50 | 0.4 | 1.56 | 12.5 | 1.56 |
| Klebsiella pneumoniae 8045 | 0.2 | 0.1 | 12.5 | ≦0.05 | 0.78 | 3.12 | 0.78 |
| Klebsiella pneumoniae Y-60 | 6.25 | 12.5 | 50 | 0.78 | 12.5 | 50 | 3.12 |
| Serratia marcescens T-55 | 6.25 | 3.12 | >100 | 1.56 | 6.25 | 50 | 50 |
| Proteus mirabilis 1287 | 3.12 | 1.56 | 12.5 | 0.1 | 3.12 | 25 | 12.5 |
| Proteus vulgaris 6897 | 100 | ≦0.05 | 25 | 0.4 | 100 | 25 | 12.5 |
| Proteus morganii KY4298 | >100 | 3.12 | >100 | 0.4 | >100 | >100 | >100 |
| Pseudomonas putida F264 | 100 | 25 | >100 | 3.12 | 100 | >100 | >100 |
| Proteus rettgeri KY4289 | 100 | 3.12 | 25 | 0.1 | 100 | >100 | 25 | a: The compound (A) obtained in Ex. 2.
b: The compound obtained in Ex. 4.
c: The compound obtained in Ex. 7.
d: The compound obtained in Ex. 9.
e: The compound obtained in Ex. 10.
f: Cephalexin
g: Cefazolin

What is claimed is:

1. A carbacephem compound represented by the formula:

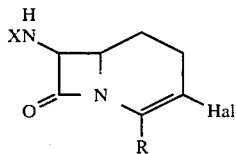

wherein

R is a carboxylic acid or a salt thereof;

Hal represents a halogen atom; and

X represents an acyl group of the formula $X_2CO$, wherein $X_2$ is selected from the group consisting of cyanomethyl or a group represented by the formula:

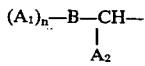

wherein B represents an unsaturated six membered carbocycle, or a five or six membered heterocyclic group wherein the heterocyclic group is monocyclic and selected from the group consisting of heterocyclic groups having 1 to 4N heteroatoms, heterocyclic groups having one S or O heteroatom and heterocyclic groups having one S or O heteroatom and one or two N heteroatoms; $A_1$ represents a substituent(s) on B selected from the group consisting of hydrogen, hydroxyl, lower alkoxy having 1 to 4 carbons, halo, nitro, amino, aminomethyl, methylsulfonamido and lower acyloxy having 1 to 4 carbons; n is an integer from 0 to 5; and $A_2$ is selected from the group consisting of hydrogen, amino, hydroxyl, carboxyl and sulfo.

2. The carbacephem compound of claim 1, wherein the carbocycle is selected from the group consisting of cyclohexenyl, cyclohexadienyl and phenyl.

3. The carbacephem compound of claim 1, wherein the heterocycle is selected from the group consisting of furyl, thienyl, pyrrolyl, thiazolyl, oxazolyl, isothiazolyl, isoxazolyl, imidazolyl, pyrozolyl, triazolyl, tetrazolyl, pyridinyl, pyrimidinyl, pyrazinyl, pyridazinyl, triazinyl and 5,6-dihydro-1-4-dithiin-2-yl.

4. The carbacephem compound of claim 1, wherein R is carboxylic acid and X is

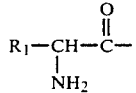

wherein $R_1$ is substituted or unsubstituted phenyl and the substituent(s) is hydroxyl, halogen or methansulfonamido.

5. A pharmaceutical composition, comprising a carbacephem compound of claim 1 and a pharmacologically acceptable carrier.

6. A pharmaceutical composition, comprising a carbacephem compound of claim 2 and a pharmacologically acceptable carrier.

7. A pharmaceutical composition, comprising a carbacephem compound of claim 3 and a pharmacologically acceptable carrier.

8. A pharmaceutical composition, comprising a carbacephem compound of claim 4 and a pharmacologically acceptable carrier.

9. (6R,7S) 7-(R)-phenylglycinamido-3-chloro-1-azabicyclo[4,2,0]oct-2-en-8-on-2-carboxylic acid.

10. (6R,7S) 7-(R)-p-hydroxyphenylglycinamido-3-chloro-1-azabicyclo[4,2,0]oct-2-en-8-on-2-carboxylic acid.

11. A pharmaceutical composition, comprising the compound of claim 9 and a pharmacologically acceptable carrier.

12. A pharmaceutical composition, comprising the compound of claim 10 and a pharmacologically acceptable carrier.

13. The pharmaceutical composition of claim 5, wherein said pharmacologically acceptable carrier is a solid.

14. The pharmaceutical composition of claim 6, wherein said pharmacologically acceptable carrier is a solid.

15. The pharmaceutical composition of claim 7, wherein said pharmacologically acceptable carrier is a solid.

16. The pharmaceutical composition of claim 8, wherein said pharmacologically acceptable carrier in a solid.

17. The pharmaceutical composition of claim 11, wherein said pharmacologically acceptable carrier is a solid.

18. The pharmaceutical composition of claim 12, wherein said pharmacologically acceptable carrier is a solid.

* * * * *

UNITED STATES PATENT AND TRADEMARK OFFICE
CERTIFICATE OF CORRECTION

PATENT NO. : 4,708,956

DATED : November 24, 1987

INVENTOR(S) : TADASHI HIRATA, ET AL.

Page 1 of 4

It is certified that error appears in the above-identified patent and that said Letters Patent is hereby corrected as shown below: On the Title Page

AT [56] IN THE REFERENCES - OTHER PUBLICATIONS

"Guth, Konda et al," should read --Guthikonda et al.,--.

Insert: --Hirata, et al., Chem. Abstracts 93, 239247t (1980);
Hirata, et al., Chem. Abstracts 94, 121355u (1980);
Hirata, et al., Chem. Abstracts 94, 101305z (1980);
Uyeo et al., Chem. Pharm. Bull. 28, 1563 (1980)--.

COLUMN 1

Line 32, "(i)-1-carbacephalotin" should read --($\pm$)-1-carbacephalotin--.

COLUMN 2

Line 28, "acrylat-" should read --acylat---.

COLUMN 5

Line 52, "(anci)" should read --(anti)--.

COLUMN 6

Line 44, "acrylation" should read --acylation--.

COLUMN 7

Line 40, "$(A'_1)_n B$" should read --$(A'_1)_n B$--.

UNITED STATES PATENT AND TRADEMARK OFFICE
CERTIFICATE OF CORRECTION

PATENT NO. : 4,708,956
DATED : November 24, 1987
INVENTOR(S) : TADASHI HIRATA, ET AL.

It is certified that error appears in the above-identified patent and that said Letters Patent is hereby corrected as shown below:

COLUMN 8

Line 2, "an active" should read --an inactive--.

COLUMN 11

Lines 56-57, ") O↑ Sph" should read -- \O↑ Sph --.

COLUMN 13

Line 50, "31 15°" should read ---15°--.

COLUMN 15

Line 20, "sialica;" should read --silica;--.
Line 46, "desires should read --desired--.

COLUMN 16

Lines 63-64, "H \" should read --H /\ --.

COLUMN 17

Line 36, "ore" should read --or--.
Line 49, "2en" should read --2-en--.

UNITED STATES PATENT AND TRADEMARK OFFICE
CERTIFICATE OF CORRECTION

PATENT NO. : 4,708,956
DATED : November 24, 1987
INVENTOR(S) : TADASHI HIRATA, ET AL.

It is certified that error appears in the above-identified patent and that said Letters Patent is hereby corrected as shown below:

COLUMN 18

Line 34, "185," should read --1785,--.

COLUMN 19

Line 35, insert --Melting point: 175-190°C (slow decomposition)--.

COLUMN 20

Line 50, "137' C." should read --137° C.--.
Line 52, "$J_{32}$ 1.7" should read --J=1.7--.

COLUMN 21

Line 47, "2en" should read --2-en--.

COLUMN 22

Line 43, "form" should read --from--.
Line 45, "hydroxyphenylc-" should read --hydroxyphenylg---.
Line 54, "rein" should read --resin--.

UNITED STATES PATENT AND TRADEMARK OFFICE
CERTIFICATE OF CORRECTION

PATENT NO. : 4,708,956

DATED : November 24, 1987

INVENTOR(S) : TADASHI HIRATA, ET AL.

It is certified that error appears in the above-identified patent and that said Letters Patent is hereby corrected as shown below:

COLUMN 24

Line 61, "in" should read --is--.

Signed and Sealed this

Twenty-eighth Day of June, 1988

Attest:

DONALD J. QUIGG

Attesting Officer

Commissioner of Patents and Trademarks

UNITED STATES PATENT AND TRADEMARK OFFICE

CERTIFICATE EXTENDING PATENT TERM
UNDER 35 U.S.C. § 156

PATENT NO.: 4,708,956

DATED: November 24, 1987

INVENTORS: Tadashi Hirata et al.

PATENT OWNER: Kyowa Hakko Kogyo Co., Ltd.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

402 DAYS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks